United States Patent
Bedbury et al.

(10) Patent No.: US 6,541,651 B1
(45) Date of Patent: Apr. 1, 2003

(54) PROCESS FOR CHLOROSILANE INTERMEDIATES MANUFACTURE

(75) Inventors: Curtis J. Bedbury, Midland, MI (US); John P. Cannady, Midland, MI (US); Binh T. Nguyen, Midland, MI (US)

(73) Assignee: Dow Corning Corporation, Midland, MI (US)

(*) Notice: Subject to any disclaimer, the term of this patent is extended or adjusted under 35 U.S.C. 154(b) by 0 days.

(21) Appl. No.: 10/116,885

(22) Filed: Apr. 4, 2002

(51) Int. Cl.$^7$ .................................................. C07F 7/08
(52) U.S. Cl. ................................. 556/480; 260/665 G
(58) Field of Search ....................... 260/665 G; 532/480

(56) References Cited

U.S. PATENT DOCUMENTS

| | | | |
|---|---|---|---|
| 2,795,627 A | 6/1957 | Ramsden | |
| 2,795,628 A | 6/1957 | Ramsden | |
| 3,095,460 A | 6/1963 | Olah | |
| 4,127,507 A | * 11/1978 | Fannin et al. | 260/655 G |
| 5,099,040 A | * 3/1992 | Rosen et al. | 260/665 G UX |
| 5,596,120 A | 1/1997 | Bank et al. | |
| 6,057,480 A | * 5/2000 | Ueno et al. | 260/665 G |

OTHER PUBLICATIONS

Tuulmets, et al., Partially Solvanted Alkylmagnesium Chlorides in Toluene, Jur. of Organometallic Chem., 523 (1966) pp. 133–138.

Tuulments, et al., Solvation Effects in Partially Solvated Grignard Reagents, Jour. of Organometalic Chem. 575 (1999) pp. 182–186.

* cited by examiner

*Primary Examiner*—Paul F. Shaver
(74) *Attorney, Agent, or Firm*—Robert L. McKellar

(57) ABSTRACT

Processes for the preparation of phenyl Grignard reagents in co-solvents of toluene and ether and, the preparation of phenylchlorosilane intermediates using co-solvents of toluene and ether essentially in a one step process. The phenylchlorosilanes in the processes of this invention are important intermediates for the preparation of various silicone materials.

20 Claims, No Drawings

PROCESS FOR CHLOROSILANE INTERMEDIATES MANUFACTURE

The invention disclosed herein deals with processes for the preparation of phenyl Grignard reagents in co-solvents of toluene and ether and, the preparation of phenylchlorosilane intermediates using co-solvents of toluene and ether essentially in a one step process. The phenylsilanes in the processes of this invention are important intermediates for the preparation of various silicone materials.

BACKGROUND OF THE INVENTION

The use of basic Grignard reagents is old in the art and originally consisted of the reaction of organomagnesium halides with compounds having active hydrogen. The reagents were prepared by combining the desirable halide in absolute ether with metallic magnesium and without having to remove the solvent, the reagent was then further reacted with the compounds having the active hydrogens.

Typically, all Grignard reagent preparations are carried out in ether as the solvent. The reactions require careful attention to the volatility of the ether and therefore, care must be taken in the handling of the reagents and their eventual reaction conditions.

When the Grignard reagents are used in the preparation of chlorosilanes, one byproduct of the reaction is magnesium salts, which are quite soluble in the ether solvent or they form complexes with ether, for example diethyl ether, and are therefore not easily susceptible to complete removal from the intermediate that has been formed.

For example, in current processes for the preparation of $PhMeSiCl_2$, (phenylmethyldichlorosilane), a very highly desirable intermediate, the Grignard reagent PhMgCl is formed in diethylether and then is coupled with $MeSiCl_3$ in diethyl ether/toluene co-solvent to form the phenylchlorosilane intermediate. It should be noted that this is a two step process to obtain the phenylchlorosilane. The majority of by-product in this reaction is $MgCl_2$ that is a very fine, solid powder that is highly soluble in the ether.

Earlier attempts at preparing the $PhMeSiCl_2$ on a commercial scale were beset by problems directly associated with the ability to remove the $MgCl_2$ and separate it from the desired product. This necessitated the use of large volumes of solvent and created other operational problems in the separation process. Usually, upon the distillation separation of the solvents and the formed intermediates, there always resulted a small amount, on the order of about 1 to 2 weight percent, of residual $MgCl_2$ and this created the need to find some way to remove this material from the final product.

The inventive processes disclosed herein have as one benefit, a one step process for the production of phenylchlorosilanes which includes the preparation of the precursor Grignard reagent, along with the capability for efficient removal of the $MgCl_2$ formed by the reaction, and further, there is a benefit of higher selectivity for the formation of the desired phenylchlorosilane intermediates and the efficient removal of $MgCl_2$ therefrom.

PRIOR ART

Methods are known in the prior art to prepare Grignard reagents containing phenyl groups and methods are known in the prior art to prepare Grignard reagents containing methyl groups.

For example, U.S. Pat. No. 2,795,627 that issued in June of 1957 deals with the preparation of phenyl Grignard reagents using chlorobenzene, magnesium and a halide catalyst, while U.S. Pat. No. 2,795,628 which also issued in June of 1957 deals with the use of chlorobenzene and magnesium at reflux temperatures to provide phenyl Grignard reagents.

In addition, OLah, in U.S. Pat. No. 3,095,460, which issued June, 1963 discloses the use of magnesium and alkylchlorides in various solvents to prepare stabilized magnesium alkyl compounds that do not use highly flammable solvents.

Tuulmets, et al., in "Partially Solvated Alkylmagnesium Chlorides in Toluene", *Journal of Organometallic Chemistry*, 523 (1996) pp. 133–138, and Tuulmets, et al., "Solvation Effects in Partially Solvated Grignard Reagents, *Jounal of Organometallic Chemistry*, 575 (1999) pp.182–186, deal with the preparation of alkylmagnesium chlorides and diethylether/toluene co-solvent solutions.

Finally, Bank, et al, in U.S. Pat. No. 5,596,120, that issued Jan. 21, 1997, deals with the preparation of organosilanes in which preparation, the reaction is a one step process that comprises contacting magnesium metal with a mixture comprising an organic halide and a halosilane in a co-solvent comprising about one to fifteen moles of a dialkyl ether per mole of allyl chloride and about 0.05 to less than two moles of a liquid aromatic hydrocarbon solvent per mole of the dialkyl ether at a temperature within a range of about 5° C. to about 200° C. The hydrocarbon solvents are shown as toluene, xylene, and benzene with the preferred solvent being toluene. The organosilanes are shown as methyl-containing silanes, and no mention is made of this process to prepare phenylchlorosilanes.

THE INVENTION

What is disclosed as the invention herein is a process for the preparation of phenyl containing Grignard reagents in novel solvent mixtures comprised of a combination of dialkyl ethers and toluene, which, in another embodiment of this invention, are used to prepare phenylchlorosilanes. The processes of this invention lead to beneficial process efficiencies by allowing a one step process for the preparation of the phenylchlorosilanes and thereafter, the removal of any solids formed during the reaction in the process, along with higher selectivity for the desired intermediates, and a faster reaction in the formation of the intermediates along with the reduction in the volume of waste products associated with the one step process.

Thus, one embodiment of the invention disclosed and claimed herein is a process for the preparation of phenyl-containing Grignard reagents, the process comprising contacting magnesium metal with a phenylhalide in the presence of a co-solvent comprised of toluene and a dialkyl ether to form phenylmagnesiumhalide.

In a second embodiment, there is a process for the preparation of a chlorosilane, the process comprising contacting magnesium metal with a mixture comprising a phenylhalide wherein the halide is selected from chlorine and bromine, and coupling the formed Grignard product with a chlorosilane having the general formula $R_aSiX_{4-a}$ wherein each R is independently selected from the phenyl group, the methyl group, the vinyl group, and hydrogen, X is chlorine or bromine, and $_a$ has a value of 0, 1, or 2, and in the presence of a co-solvent comprising a mixture of a dialkyl ether and toluene. After the reaction is essentially complete, the formed intermediate is separated from essentially all of any solids formed during the reaction.

With regard to the first embodiment of this invention, and with more specific detail, the process deals with the preparation of a phenyl-containing Grignard reagent wherein the process is carried out in a co-solvent mixture of toluene and a dialkyl ether.

The magnesium metal useful in this invention can be any of the known forms of the metal that are currently used for Grignard-type reactions. For example, the metal can be any of those known in the art that are in the form of powder, flakes, granules, chips, lumps, and shavings, and the like.

Contact of the magnesium metal with the phenylhalide can be undertaken in standard type reactors suitable for running Grignard type reactions. The reactor can be a batch, semi-batch, or continuous type of reactor. A preferred reactor is a continuous reactor. The environment in which the present method is carried out should be inert for best results. Therefore, in a preferred method, the reactor is purged and blanketed with an inert gas such as, for example, nitrogen or argon.

Generally, the magnesium metal is fed into a reactor containing the co-solvent mixture. The phenyl halide in additional co-solvent is also fed to the reactor at a controlled rate. The mole ratio of magnesium to the phenyl halide fed to the reactor is not critical and can be varied within wide limits. In a batch process, it is preferred that the final mole ratios of magnesium to phenyl halide provide the phenyl halide in sufficient excess to ensure essentially total conversion of the magnesium to the magnesium salts.

When the present process is conducted as a continuous process, the magnesium metal is typically present in excess in relation to the phenyl halide fed to the reactor. In such a case, the rate of feed of the phenyl halide to the reactor can be controlled to ensure acceptable levels of conversion of the phenyl halide to the desired compounds and minimize the presence of the unreacted phenyl magnesium halide complexes. Any excess of the phenyl halide can be captured and recycled to the reactor.

Phenyl halides useful in this invention are those described by the formula RX, wherein R is phenyl and X is selected from chlorine or bromine atoms. Preferred for this invention is phenyl chloride.

The dialkyl ether useful in this invention includes, for example, dimethyl ether, diethyl ether, ethylmethyl ether, n-butylmethyl ether, n-butylethyl ether, di-n-butyl ether, di-isobutyl ether, isobutylmethyl ether, and isobutylethyl ether, and the like. The preferred ether is diethyl ether.

It is preferred that the amount of toluene in the co-solvent mixture be as large as is possible. The present process requires that the amount of toluene that is present be as high as is possible, meaning that a high ratio of the toluene to the ether is desired. This is because it is believed by the inventors herein that the toluene aids in the precipitation of the very fine $MgCl_2$ that is formed during the reaction and substantially aids in the removal of such salts. Thus, for purposes of this method, the ratio of the total ether to the toluene should in the range of about 0.05:1.0 to 2:1.

In the second embodiment of this invention, the phenyl Grignard reagent that is prepared as set forth above, in ether/toluene co-solvent is used to prepare the phenyl-containing silanes. The present invention is one in which the phenyl Grignard reagent and the phenyl-containing silane are prepared essentially simultaneously by feeding the precursor silane to the reactor as the phenyl Grignard reagent is being made. Thus, the process results in a one step process starting from the feeding of the magnesium metal and ending with the final silane product.

The most desirable phenyl-containing silanes prepared by this inventive process are phenylmethyldichlorosilane and diphenylmethylchlorosilane. The following chemical reactions are suggested, wherein Ph is phenyl, Mg is magnesium, Me is methyl, Si is silicon, and Cl is the halide used.

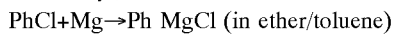

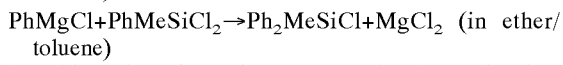

When this series of reactions were undertaken using just ether as the solvent to prepare the Grignard reagent and the silane, high volumes of additional side products were also made resulting is as much as 0.5 pounds of waste per 1 pound of, for example, $PhMeSiCl_2$. The inventive process herein allows for the preparation of $PhMeSiCl_2$, for example wherein the waste is at or less than 0.2 pounds for each pound of silane prepared, a reduction in waste of approximately 50 to 60%.

Typically the temperature range in which this process is carried out is in the range of from 5° C. to 200° C., and most preferred range is from about 50° C. to about 100° C., and the pressure is in the range of from ambient pressure to about 200 psig wherein the most preferred range is from 0 psig to about 125 psig.

EXAMPLE

Preparation of Phenylmethyldichlorosilane and Diphenylmethylchlorosilane

The process was carried out in a continuous process in a reactor that would allow the direct fed of the substituents to the reactor. The reaction is started by feeding magnesium, phenylCl and diethyl ether to the Grignard reactor and then followed by a feed of $MeSiCl_3$ and toluene in the coupling reaction.

The ether and phenylCl are fed in a ratio of 4:1 and the magnesium is fed at a rate to sustain the reaction as monitored by the reactor temperature profile, jacket water temperature rise, and agitator motor amps. The $MeSiCl_3$ feed is varied to obtain a coupling ratio between 0.25 and 0.90 moles of PhCl/mole of $MeSiCl_3$ depending on the ratio of $Ph_2SiMeCl/PhMeSiCl_2$ desired. Toluene is fed in at a 3:1 ratio to the PhenylCl in ether.

A rotameter was inserted into the toluene feed line to control a continuous flow to obtain a targeted toluene concentration in the diethyl ether.

After the Grignard reaction smoothed out, toluene was added to the reactor to raise the toluene level to 5 weight percent in ether. The PhenylCl was running at 55 gallons per hour, the ether/toluene mixture was running at 226 gals per hour and the magnesium at 105 to 110 lbs/hour. The temperature in the Grignard reactor varied from 118° C. to 160° C. and the heat of reaction as measure by the jacket water temperature rise was 0.60 to 0.80 MM BTU per hours. The agitator motor was drawing 14 to 19 amps indicating fairly normal operation. The temperature of the coupler reactor was at 85 to 90° C. Any ether leaving the reaction was recovered and recycled to the reactor, and additional toluene was added to keep the level at or near 5%. The reaction was run on a continuous basis for several hours at this toluene level to test out the reaction results before moving to a higher toluene level.

At 48 hours of run time, the toluene level in the ether feed to the Grignard reactor was adjusted to 10% and 24 hours later, the toluene level was increased to 20% and the reactors were allowed to run for the next 72 hours. After a minor shutdown the reaction was restarted and the toluene level was raised to 30%. The toluene level was increased to 40% after 120 hours of operation and then at the 40% level, the reactor was allowed to run for 72 additional hours. Analysis of the crude Grignard product showed the waste ratio to PhMeSiCl$_2$ was at 0.2.

What is claimed is:

1. A process for the preparation of phenyl-containing Grignard reagents, the process comprising contacting magnesium metal with a phenylhalide in the presence of a co-solvent comprised of a mixture of dialkyl ether and toluene.

2. A process as claimed in claim 1 wherein the process is carried out at a temperature of about 5° to about 200°.

3. A process as claimed in claim 1 wherein the process is carried out at a pressure of about ambient to 200 psig.

4. A process as claimed in claim 1 wherein the process is carried out in an inert atmosphere.

5. A process as claimed in claim 4 wherein the inert atmosphere is nitrogen.

6. A process as claimed in claim 1 wherein the ratio of dialkyl ether to toluene is 0:1 to 2:1.

7. A process as claimed in claim 1 wherein the phenylhalide is phenylchloride.

8. A process as claimed in claim 1 wherein the phenylhalide is phenylbromine.

9. A process as claimed in claim 1 wherein the dialkyl ether is diethyl ether.

10. A process for the preparation of a phenylchlorosilane the process comprising contacting magnesium metal with a mixture comprising:

i. a phenylhalide wherein the halide is selected from chlorine and bromine;

ii a chlorosilane having the general formula R$_a$SiX$_{4-a}$ wherein each R is independently selected from the phenyl group, the methyl group, the vinyl group and hydrogen, X is chlorine or bromine, and $_a$ has a value of 0,1, or 2;

iii a co-solvent comprising a dialkyl ether and toluene.

11. A process as claimed in claim 10 wherein the volume ratio of the dialkyl ether solvent to the toluene is in the range of 0.05:1 to 10:1.

12. A process as claimed in claim 10 wherein the process is carried out at a temperature of about 5° C. to about 200°.

13. A process as claimed in claim 10 wherein the process is carried out at a pressure of about 0 to 125 psig.

14. A process as claimed in claim 10 wherein the process is carried out in an inert atmosphere.

15. A process as claimed in claim 14 wherein the inert atmosphere is nitrogen.

16. A process as claimed in claim 10 wherein the ratio of dialkyl ether to toluene is 0.5:1 to 5:1.

17. A process as claimed in claim 10 wherein the phenylhalide is phenylchloride.

18. A process as claimed in claim 10 wherein the phenylhalide is phenylbromide.

19. A process as claimed in claim 10 wherein the dialkyl ether is diethyl ether.

20. A process as claimed in claim 10 wherein chlorosilane is selected from the group consisting of silicon tetrachloride, methyltrichlorosilane, dimethyldichlorosilane, phenylmethyldichlorosilane, phenyltrichlorosilane, diphenyldichlorosilane, vinyltrichlorosilane, hydridotrichlorosilane, divinyldichlorosilane, methylvinyldichlorosilane, phenylvinyldichlorosilane, hydridomethyldichlorosilane, hydridophenyldichlorosilane, hydridovinyldichlorosilane and dihydridodichlorosilane.

* * * * *